(12) United States Patent
Jackson et al.

(10) Patent No.: US 8,552,222 B2
(45) Date of Patent: Oct. 8, 2013

(54) CHEMICAL PROCESS FOR THE PRODUCTION OF HALOALKENONE ETHERS

(75) Inventors: David Anthony Jackson, Münchwilen (CH); Florian Schleth, Münchwilen (CH); Devender Singh Negi, Muenchwilen (CH); Werner Pfaff, Muenchwilen (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 25 days.

(21) Appl. No.: 13/254,795

(22) PCT Filed: Mar. 2, 2010

(86) PCT No.: PCT/EP2010/001267
§ 371 (c)(1),
(2), (4) Date: Nov. 28, 2011

(87) PCT Pub. No.: WO2010/099922
PCT Pub. Date: Sep. 10, 2010

(65) Prior Publication Data
US 2012/0095265 A1      Apr. 19, 2012

(30) Foreign Application Priority Data
Mar. 4, 2009  (GB) .................................. 0903749.0

(51) Int. Cl.
*C07C 45/63*  (2006.01)
*C07C 45/64*  (2006.01)

(52) U.S. Cl.
USPC ............................ 568/392; 568/393; 568/404

(58) Field of Classification Search
USPC ................................................. 568/392, 404
See application file for complete search history.

(56) References Cited

U.S. PATENT DOCUMENTS

2006/0084813 A1 *   4/2006   Hausmann et al. ........... 546/315

FOREIGN PATENT DOCUMENTS

EP         1254883       11/2002
WO      2009/006217      1/2009

OTHER PUBLICATIONS

Tietzet et al. Synthesis of Alkyl Propanoates by a Haloform Reaction of a Trichloro Ketone: Preparation of Ethyl-3,3-Diethoxypropanoate. Organic Synthesis, 1990, vol. 69, p. 238-244.*
Effenberger et al, "Die Acylierung von Enolethern mit reaktiven Carbonsaurechloriden", Chemische Berichte, vol. 115, 1982, pp. 2766-2782.

* cited by examiner

Primary Examiner — Sikarl Witherspoon
(74) Attorney, Agent, or Firm — James Cueva

(57) ABSTRACT

The present invention relates to a continuous process for producing a haloalkenone ether of the Formula (I) wherein $R^1$ is $C_1$-$C_6$ haloalkyl, $R^2$ is a $C_1$-$C_6$ alkyl or phenyl, the process comprising:—(i) reacting, in a first continuous stirred tank reactor comprising a solvent, a halide of Formula (II) wherein $R^1$ is as previously defined and $R^3$ is halogen, with a vinyl ether of Formula (III) wherein $R^2$ is as previously defined, to form an intermediate compound of Formula (IV), wherein the concentration of the vinyl ether of Formula (III) in the reaction mass is 15% or less w/w; and (ii) transferring the reaction mass from the first continuous stirred tank reactor into a subsequent continuous stirred tank reactor, wherein the conditions within the subsequent reactor permit the elimination of hydrogen halide ($HR^3$) from the intermediate compound of Formula (IV) to provide the haloalkenone ether of Formula (I).

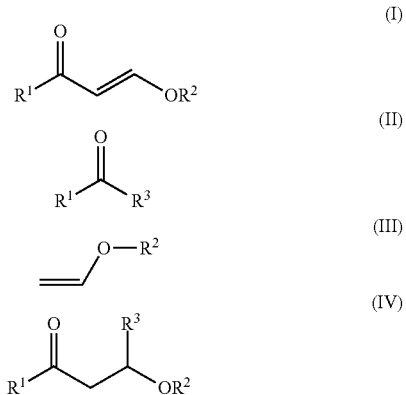

17 Claims, No Drawings

CHEMICAL PROCESS FOR THE PRODUCTION OF HALOALKENONE ETHERS

This application is a 371 of International Application No. PCT/EP2010/001267 filed Mar. 2, 2010, which claims priority to GB 0903749.0 filed Mar. 4, 2009, the contents of which are incorporated herein by reference.

The present invention relates to an improved process for the production of haloalkenone ethers, in particular 4-ethoxy-1,1,1-trifluoro-3-buten-2-one.

Processes for producing haloalkenone ethers, such as the above, are known. Thus, EP-A-1254883 describes a semi-batch process for producing haloalkenone ethers wherein the process is conducted in the presence of a base. WO2004108647 describes a semi-batch process conducted in the absence of a base and/or in the presence of a stabilizer for the resulting alkenone. However, these semi-batch processes can exhibit disadvantages in respect of larger scale, commercial production. In particular, in order to produce commercial quantities of the desired product the known semi-batch processes require the use of large reactors. Furthermore, the use of a base and/or additional solvent in the process requires, for example, additional purification steps. Still further, semi-batch processes wherein the halide is added to excess alkyl vinyl ether requires the use of large quantities the alkyl vinyl ether, which is undesirable as polymerisation of the alkyl vinyl ether can readily occur.

A new improved process has now been developed which allows the process to be conducted in continuous manner—which is more commercially desirable—and which overcomes the above-mentioned disadvantages associated with the known processes. In particular, the continuous process to which the present invention relates can, if desired, be operated in the absence of a base (or other stabilisers) and/or other reagents/solvents, allows the use of smaller reactors than a semi-batch process, provides good reaction rates and yields as the continuous process allows the use of reaction temperatures above those typically associated with the semi-batch processes, avoids storage of unstable intermediate compounds and keeps the formation of any undesirable by-products to a minimum.

Thus, according to the present invention there is provided a continuous process for producing a haloalkenone ether of Formula (I)

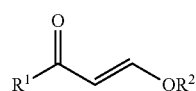

(I)

wherein $R^1$ is $C_1$-$C_6$ haloalkyl, $R^2$ is a $C_1$-$C_6$ alkyl or phenyl, the process comprising:—

(i) reacting, in a first continuous stirred tank reactor comprising a solvent, a halide of Formula (II)

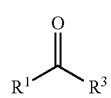

(II)

wherein $R^1$ is as previously defined and $R^3$ is halogen, with a vinyl ether of Formula (III)

(III)

wherein $R^2$ is as previously defined, to form an intermediate compound of Formula (IV),

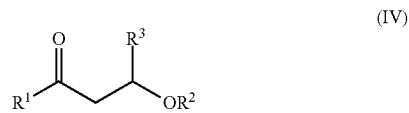

(IV)

wherein the concentration of the vinyl ether of Formula (III) in the reaction mass is 15% or less w/w; and (ii) transferring the reaction mass from the first continuous stirred tank reactor into a subsequent continuous stirred tank reactor, wherein the conditions within the subsequent reactor permit the elimination of hydrogen halide ($HR^3$) from the intermediate compound in order to provide the haloalkenone ether of the Formula (I).

In a preferred embodiment $R^1$ is selected from the group consisting of $CH_2F$, $CHF_2$, $CH_3$, $C_2H_5$ and $CF_3$. In a more preferred embodiment $R^1$ is $CF_3$.

In another preferred embodiment $R^2$ is ethyl.

In another preferred embodiment $R^3$ is chlorine.

In a particularly preferred embodiment the process is for producing 4-ethoxy-1,1,1-trifluoro-3-buten-2-one wherein $R^1$ is $CF_3$, $R^2$ is ethyl and $R^3$ is chlorine.

In order to allow the process to proceed in a continuous manner it has been found that it is important that the concentration of the alkyl vinyl ether of Formula (III) in the first continuous stirred tank reactor is 15% or less w/w, even 10% or less or even 5% or less.

The solvent in the first continuous stirred tank reactor can be any suitable solvent in which the reaction can be conducted. Examples of suitable solvents include toluene, methylene chloride and ethylene dichloride. However, in a preferred embodiment of the present invention the solvent comprises a compound of Formula (I), a compound of Formula (IV) or a mixture thereof. The use of a compound of Formula (I) and/or a compound of Formula (IV) as the solvent provides for a simplified process which avoids the need for additional solvents, avoids additional purification steps, avoids the generation of undesirable waste streams and thus offers significant cost reduction. In addition, it has been found that a faster rate of acetylation is observed in the continuous process of the present invention if a compound the Formula (I) and/or the intermediate compound of Formula (IV) are used as the solvent compared with, for example, toluene. Furthermore, where the halide of Formula (II) used in the process is a gas (for example trifluoroacetylchloride) then it has been found that this is readily soluble in a compound of Formula (I) and/or a compound of Formula (IV).

Thus, in the continuous process of the present invention the halide of Formula (II) and the vinyl ether of Formula (III) are fed into the in a first continuous stirred tank reactor. The molar ratio of the halide to the vinyl ether in the reactor is typically from 0.8:1 to 1:0.8, preferably from 0.9:1.

Typically, the feed rate into the first continuous stirred tank reactor is adjusted such that the total reactor volume exchanges from one hour to five hours.

The internal temperature of the first continuous stirred tank reactor is typically from −20° C. to +35° C., more preferably from −10° C. to +10° C.

It can be seen that the process of the present invention comprises two continuous stirred tank reactors which allows the reactor volumes can be kept to a minimum. The yield of the intermediate compound of Formula (IV) using just one continuous stirred tank reactor in which to perform the acetylation reaction can be 90% or more. However, in order to improve the yield even further it should be appreciated that the process can comprise additional reactors. For example, the reaction mass from the first stirred reaction can be transferred to one or more additional continuous stirred tank reactors prior to the reaction mass being transferred to the subsequent continuous stirred tank reactor where elimination of the hydrogen halide is performed. In a particularly preferred embodiment of the present invention the reaction mass from the first stirred reaction is transferred to a plug-flow reactor before being transferred to the subsequent continuous stirred tank reactor. By utilising one or more additional continuous stirred tank reactor(s) and/or a plug flow reactor(s) the yield of intermediate compound of Formula (IV) can be increased to 95% or more.

The internal temperature of the plug flow reactor can be the same as that of the first continuous stirred tank. However, in a preferred embodiment the internal temperature of the plug-flow reactor is from 0° C. to +35° C., more preferably from 10° C. to +35° C.—which consequently allows the reaction to proceed at a faster rate and negates the need for cooling equipment to be used in conjunction with the plug-flow reactor thus further reducing cost.

The residence time in the plug-flow reactor is typically from 15 minutes to four hours, more preferably from 30 minutes to one hour.

Once the formation of the intermediate compound of Formula (IV) has reached the desired level the reaction mass is transferred to the subsequent continuous stirred tank reactor in which the conditions are such that elimination of the hydrogen halide from the intermediate compound of Formula (IV) occurs and the haloalkenone ether of Formula (I) is formed.

It is submitted that the skilled person will readily appreciate the nature of the conditions required for elimination of the halide. Typically, hydrogen halide elimination occurs under elevated temperature, lowered pressure or a combination of both. Thus, in a preferred embodiment, the internal temperature of the subsequent continuous stirred tank reactor is from +30° C. to +150° C., more preferably +70° C. to +110° C. and most preferably from +90° C. to +100° C. Indeed, it has been found that an internal temperature in excess of +90° C. is particularly beneficial because of the shortened residence time in the reactor afforded—which avoids the formation of undesirable by-products.

As has been mentioned, the internal pressure of the subsequent continuous stirred tank reactor may be optionally lowered in order to improve elimination of the hydrogen halide. Thus, in a preferred embodiment the internal pressure of the subsequent continuous stirred tank reactor is from 0 to 500 mbar, more preferably from 250 to 350 mbar. The residence time of the reaction mass in the second reactor is typically from 15 minutes to four hours, preferably from 60 minutes to three hours. It should be further understood that the reaction mass from the subsequent continuous stirred tank reactor can be recycled through the reactor, or passed into an additional continuous stirred tank reactor if required in order to improve conversion of the intermediate compound of Formula (IV) to the haloalkenone ether of Formula (I). If an additional step is utilised then it is advantageous to lower the internal pressure of the second continuous stirred tank reactor during the recycling step to further improve the conversion.

EXAMPLES

General Procedure

A 200 mL jacketed reactor equipped with an overhead stirrer and a side outlet is filled with up to 180 mL of 4-ethoxy-1,1,1-trifluoro-3-buten-2-one or 4-chloro-4-ethoxy-1,1,1-trifluoro-2-butanone. The reactor is connected to a scrubber containing aqueous sodium hydroxide. The jacket temperature is adjusted to −10° C. and trifluoro-acetylchloride (TFAC) and ethyl vinyl ether (EVE) are simultaneously fed into the reactor with the internal temperature kept between −5 and 10° C. The total reactor volume is exchanged within two to three hours and the feed rate is adjusted accordingly. The overflowing reaction mixture is allowed to pass through a plug flow reactor (PFR) attached to the outlet of the first reactor. The residence time of the reaction mixture in the PFR is thirty minutes. The PFR is operated at room temperature. An analysis of the reaction mixture at the end of the PFR is done by both GC and NMR analysis. Usually, full consumption of EVE is found. By NMR the content of 4-ethoxy-1,1,1-trifluoro-3-buten-2-one in the reaction mixture is determined and is usually found to be below 10% after three hours or more of operation. The chemical yield for the 4-chloro-4-ethoxy-1,1,1-trifluoro-2-butanone is between 90% and 100%. Cl-IM: $^1$H-NMR (400 MHz, CDCl$_3$): δ=5.96 (dd, J=7.0, 4.5 Hz, 1H), 3.96 (dq, J=9.5, 7.0 Hz, 1H) 3.61 (dq, J=9.5, 7.0 Hz, 1H), 3.51 (dd, J=18.1, 6.5 Hz, 1H), 3.38 (dd, J=18.1, 4.5 Hz, 1H), 1.24 (t, J=7.0 Hz, 3H).

The 4-ethoxy-1,1,1-trifluoro-3-buten-2-one/4-chloro-4-ethoxy-1,1,1-trifluoro-2-butanone mixture is fed into a second jacketed reactor (200 mL volume) equipped with an overhead stirrer. The reactor is connected to a scrubber containing aqueous sodium hydroxide. At the beginning of the reaction the reactor contains 4-chloro-4-ethoxy-1,1,1-trifluoro-2-butanone and is operated at a temperature of 80° C. and at ambient pressure or at 80° C. and an internal pressure of 350 mbar. The time for the total reactor volume to be exchanged is 60 to 120 minutes; the feed rate is adjusted accordingly. The resulting overflowing reaction mixture is collected and analyzed. If the reactor is run at ambient pressure the collected material may not be fully converted and is fed into the reactor again in a second run. For this second run the reactor is operated at 350 mbar. After the run(s) the overflowing material is found to contain 75-85% of 4-ethoxy-1,1,1-trifluoro-3-buten-2-one.

4-ethoxy-1,1,1-trifluoro-3-buten-2-one: $^1$H-NMR (400 MHz, CDCl$_3$): δ=7.88 (d, J=12.6 Hz, 1H), 5.84 (d, J=12.6 Hz, 1H), 4.09 (q, J=7.0 Hz, 2H), 1.38 (t, J=7.0 Hz, 3H). $^{13}$C-NMR (100 MHz, CDCl$_3$): δ=180.8 ($J_{C-F}$=35 Hz), 168.0, 116.4 ($J_{C-F}$=290 Hz), 98.0, 69.0, 14.3. GC analysis: HP 6890, column J&W DB-5, 15 m, 530 µm diameter, inlet: 180° C., flow He: 3.5 mL/min, 9.7 kPa; detector: 30 mL H$_2$/min, Air: 400 mL/min, 300° C. Temperature program: $T_0$=50° C., ramp to 280° C., 20° C./min, hold 5 min. Retention time: Cl-IM: 8.16 min, 4-ethoxy-1,1,1-trifluoro-3-buten-2-one: 8.90 min.

Example 1

Using the above described general procedure TFAC (854 g, 6.45 mol) and EVE (419 g, 5.81 mol) were reacted to give a crude mixture of 1244 g containing 4-chloro-4-ethoxy-1,1,1-trifluoro-2-butanone. 1239 g of this mixture were converted to 4-ethoxy-1,1,1-trifluoro-3-buten-2-one in two consecutive runs (60 minutes residence time each, first at ambient pressure, second at 350 mbar) to yield 4-ethoxy-1,1,1-trifluoro-3-buten-2-one (802 g, 4.77 mol, 82%).

Example 2

Using the above described general procedure TFAC (715 g, 5.40 mol) and EVE (389 g, 5.40 mol) were reacted to give a crude mixture of 1060 g containing -chloro-4-ethoxy-1,1,1-trifluoro-2-butanone. 924 g thereof were then converted to 4-ethoxy-1,1,1-trifluoro-3-buten-2-one (90 minutes residence time at 350 mbar) to yield 4-ethoxy-1,1,1-trifluoro-3-buten-2-one (628 g, 3.74 mol, 79%).

The invention claimed is:

1. A continuous process for producing a haloalkenone ether of Formula (I):

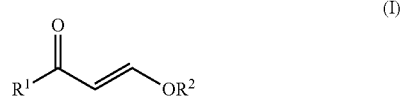
(I)

wherein $R^1$ is a $C_1$-$C_6$ haloalkyl, and $R^2$ is a $C_1$-$C_6$ alkyl or phenyl, the process comprising:
(i) reacting, in a first continuous stirred tank reactor comprising a solvent, a halide of Formula (II):

(II)

wherein $R^3$ is a halogen, with a vinyl ether of Formula (III):

(III)

to form an intermediate compound of Formula (IV):

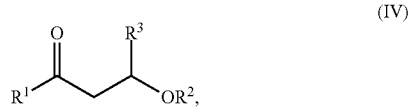
(IV)

wherein a concentration of the vinyl ether of Formula (III) in a reaction mass of said reacting step is 15% or less w/w; and (ii) transferring the reaction mass from the first continuous stirred tank reactor into a subsequent continuous stirred tank reactor, wherein conditions within the subsequent reactor permit elimination of hydrogen halide ($HR^3$) from the intermediate compound of Formula (IV) to provide the haloalkenone ether of Formula (I).

2. A process according to claim 1, wherein the concentration of the vinyl ether of Formula (III) in the reaction mass is 10% or less w/w.

3. A process according to claim 1, wherein the solvent in the first continuous stirred tank reactor is (i) a compound of Formula (I), (ii) a compound of Formula (IV), or a mixture of (i) and (ii).

4. A process according to claim 1, wherein $R^1$ is selected from the group consisting of $CH_2F$, $CHF_2$, $CH_3$, $C_2H_5$ and $CF_3$.

5. A process according to claim 4, wherein $R^1$ is $CF_3$.

6. A process according to claim 1, wherein $R^2$ is ethyl.

7. A process according to claim 1, wherein $R^3$ is chlorine.

8. A process according to claim 1, wherein an internal temperature of the first continuous stirred tank reactor is from −20° C. to +35° C.

9. A process according to claim 8, wherein the internal temperature of the first continuous stirred tank reactor is from −10° C. to +10° C.

10. A process according to claim 1, wherein the reaction mass from the first continuous stirred tank reactor is transferred to a plug-flow reactor before being transferred to the subsequent continuous stirred tank reactor.

11. A process according to claim 10, wherein a residence time in the plug-flow reactor is from 15 minutes to three hours.

12. A process according to claim 10, wherein an internal temperature of the plug-flow reactor is from 0° C. to +35° C.

13. A process according to claim 1, wherein an internal temperature of the subsequent continuous stirred tank reactor is from +30° C. to +150° C.

14. A process according to claim 13, wherein the internal temperature of the subsequent continuous stirred tank reactor is from +90° C. to +100° C.

15. A process according to claim 1, wherein an internal pressure of the subsequent continuous stirred tank reactor is from 0 to 500 mbar.

16. A process according to claim 3, wherein the concentration of the vinyl ether of Formula (III) in the reaction mass of said reacting step is 10% or less w/w.

17. A process according to claim 1, wherein the concentration of the vinyl ether of Formula (III) in the reaction mass of said reacting step is 5% or less w/w.

* * * * *